(12) United States Patent
Shao et al.

(10) Patent No.: US 7,117,026 B2
(45) Date of Patent: Oct. 3, 2006

(54) PHYSIOLOGICAL MODEL BASED NON-RIGID IMAGE REGISTRATION

(75) Inventors: Lingxiong Shao, Saratoga, CA (US); Jinghan Ye, Fremont, CA (US); Angela J. Da Silva, Danville, CA (US); Zuo Zhao, Mountain View, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 595 days.

(21) Appl. No.: 10/167,621

(22) Filed: Jun. 12, 2002

(65) Prior Publication Data

US 2003/0233039 A1 Dec. 18, 2003

(51) Int. Cl.
*A61B 5/05* (2006.01)

(52) U.S. Cl. ........................ 600/411; 600/407
(58) Field of Classification Search ............... 600/411, 600/410, 407, 414, 415, 416, 424, 425, 426, 600/1, 2, 3, 4, 5, 6, 7, 8; 324/306, 307, 308, 324/309
See application file for complete search history.

(56) References Cited

U.S. PATENT DOCUMENTS

| | | | | |
|---|---|---|---|---|
| 4,920,969 | A | * 5/1990 | Suzuki et al. | 600/436 |
| 5,007,427 | A | * 4/1991 | Suzuki et al. | 600/436 |
| 5,111,818 | A | * 5/1992 | Suzuki et al. | 600/390 |
| 5,672,877 | A | 9/1997 | Liebig | |
| 6,125,164 | A | 9/2000 | Murphy | |
| 6,132,372 | A | * 10/2000 | Essen-Moller | 600/431 |
| 6,205,347 | B1 | 3/2001 | Morgan | |
| 6,447,448 | B1 | * 9/2002 | Ishikawa et al. | 600/300 |
| 6,640,130 | B1 | * 10/2003 | Freeman et al. | 600/474 |
| 6,650,927 | B1 | * 11/2003 | Keidar | 600/424 |
| 6,659,949 | B1 | * 12/2003 | Lang et al. | 600/438 |
| 6,748,259 | B1 | * 6/2004 | Benaron et al. | 600/476 |

OTHER PUBLICATIONS

O'Donnell, Thomas, et al.; Global Models with Parametric Offsets as Applied to Cardiac Motion Recovery; IEEE, 1986, pp. 293–299.

O'Donnell, Thomas, et al.; Multi–Modality Model–Based Registration in the Cardiac Domain; IEEE, 2000, pp. 790–791.

W. P. Segars, Ph.D. thesis entitled "Development and Application of the New Dynamic NURBS–Based Cardiac Torso (NCAT) Phantom", Dept. of Biomedical Engineering, University of North Carolina at Chapel Hill, 2001.

W. Paul Segars, David S. Lalush, Benjamin M. W. Tsui "Modeling Respiratory Mechanics in the MCAT and Spline-Based MCAT Phantoms", Dept. of Biomedical Engrg. and Dept. of Radiology, U. of North Carolina at Chapel Hill; IEEE Transactions on Nuclear Science, vol. 48, No. 1, Feb. 2001, pp. 89–97.

W. Paul Segars, David S. Lalush, Benjamin M. W. Tsui "A Realistic Spline–Based Dynamic Heart Phantom", IEEE Transactions on Nuclear Science, vol. 46, No. 3, Jun. 1999; pp. 503–506.

M.F. Santarelli, V. Positano, P. Marcheschi, L. Landini, P. Marzullo, A. Benassi "Multimodal Cardiac Image Fusion by Geometrical Features Registration and Warping", Computers in Cardiology 2001; 28:277–280.

* cited by examiner

*Primary Examiner*—Daniel Robinson

(57) ABSTRACT

A method for non-rigid registration and fusion of images with physiological modeled organ motions resulting from respiratory motion and cardiac motion that are mathematically modeled with physiological constraints. A method of combining images comprises the steps of obtaining a first image dataset (24) of a region of interest of a subject and obtaining a second image dataset (34) of the region of interest of the subject. Next, a general model of physiological motion for the region of interest is provided (142). The general model of physiological motion is adapted with data derived from the first image data set (140) to provide a subject specific physiological model (154). The subject specific physiological model is applied (172) to the second image dataset (150) to provide a combined image (122).

24 Claims, 8 Drawing Sheets

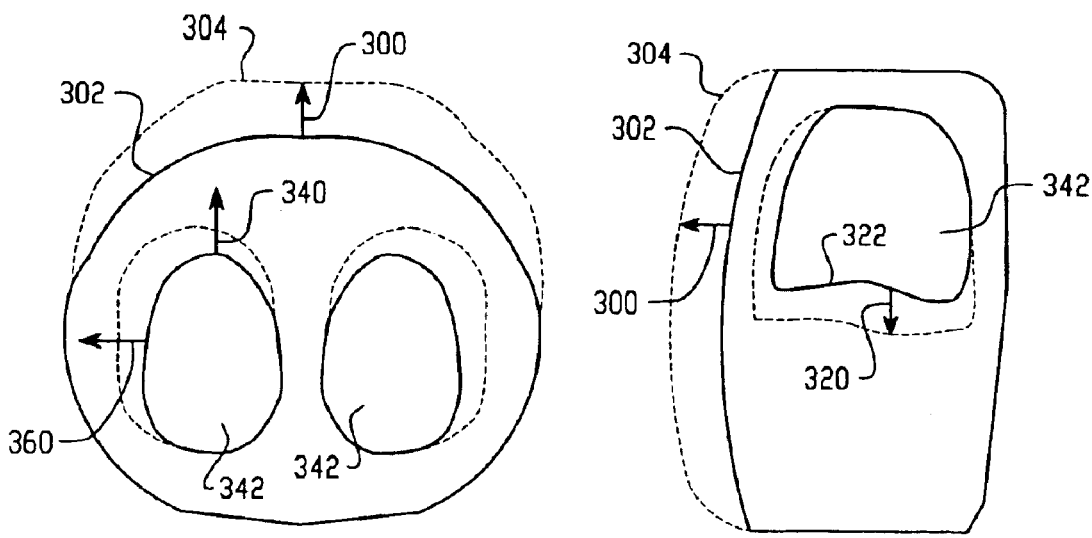
Fig. 7A  Fig. 7B
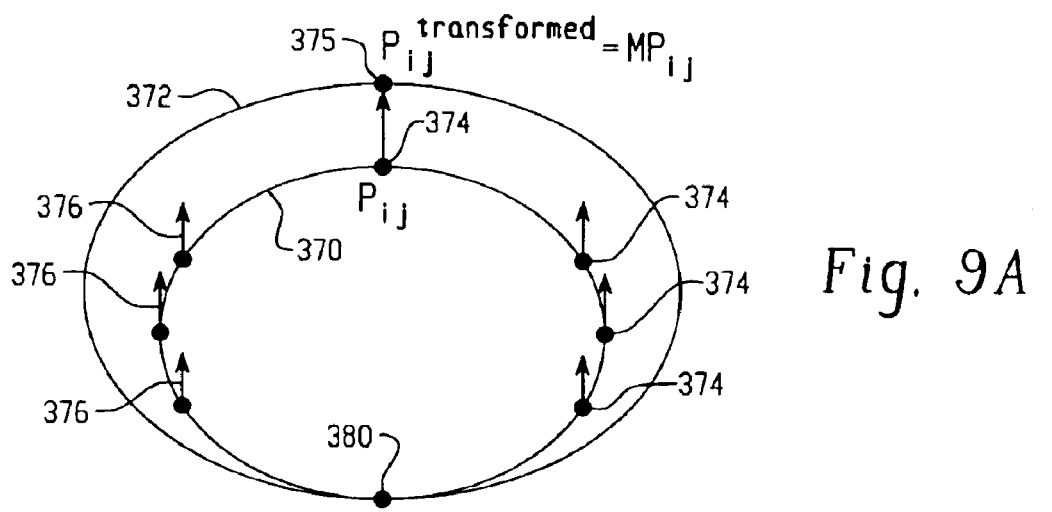
Fig. 9A
Fig. 9B

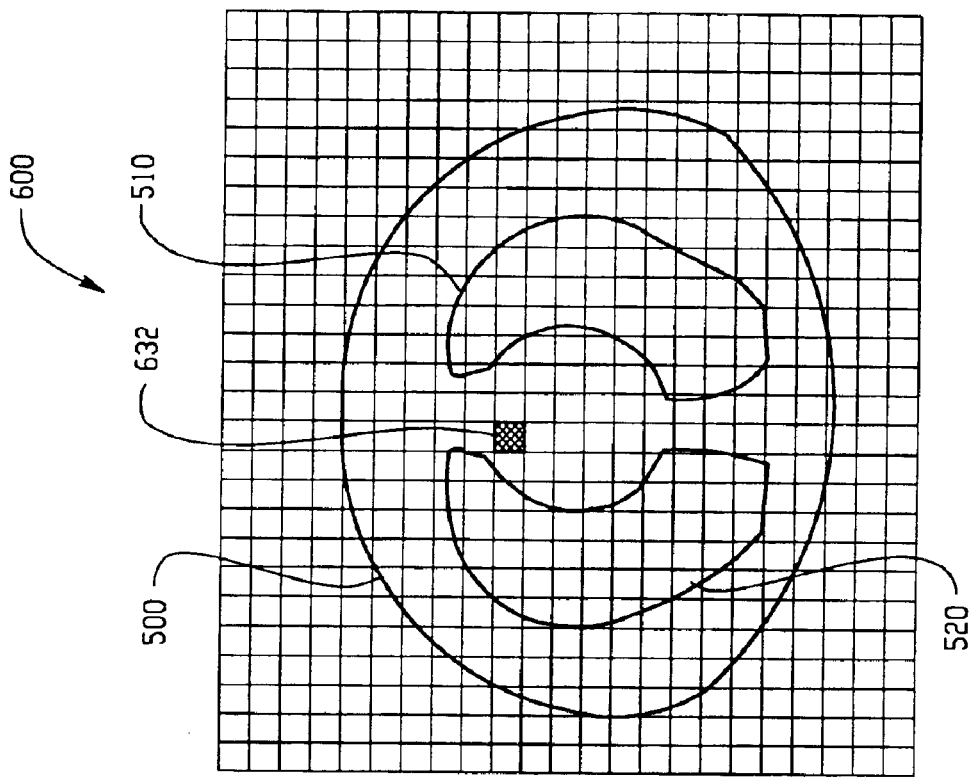
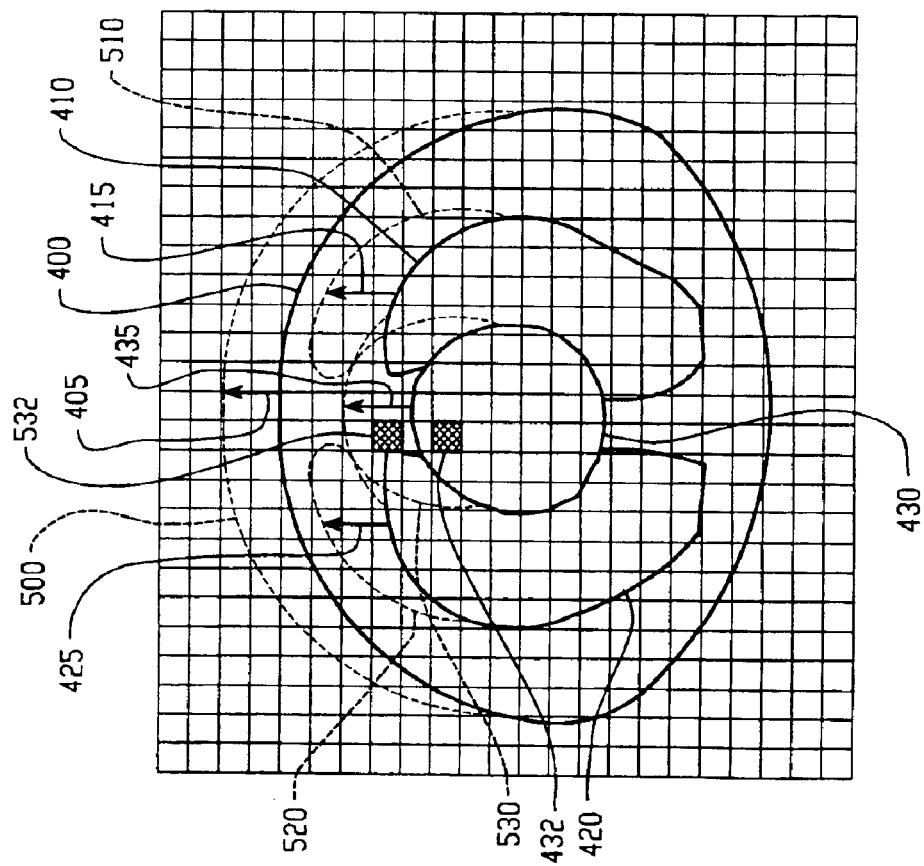
Fig. 10A
Fig. 10B

PHYSIOLOGICAL MODEL BASED NON-RIGID IMAGE REGISTRATION

BACKGROUND

The present invention relates to image registration and fusion and is particularly related to a method and apparatus using a non-rigid technique for registration and fusion of images. More specifically, the image registration and fusion is adapted to compensate for physiological motion during imaging. The present invention finds particular application in conjunction with diagnostic medical imaging and will be described with particular respect thereto.

In the practice of medicine, various techniques or imaging modalities are available for obtaining diagnostic images of the human body. Each of the imaging modalities may employ different methods and apparatus for acquiring data from an imaging subject and processing the acquired data into suitable images. The various imaging modalities yield images having features that are characteristic to the specific imaging technique.

Since the different imaging modalities have characteristic features related to their particular data acquisition and image processing methods, a particular modality may be more useful for obtaining specific types of diagnostic information. For example, functional imaging modalities include scintigraphy, functional MRI (fMRI) and nuclear medicine imaging techniques such as SPECT and PET. In addition, some lesser used functional techniques include perfusion MRI (pMRI), functional CT (fCT), electro impedance tomography (EIT) and magnetic resonance elastography (MRE). These functional modalities can provide imaging information showing primarily metabolic or functional information and some structural features of the imaged subject matter. However, images generated using some of these modalities is generally directed to a specific region, physiological system or organ of interest and yields little information about specific anatomical structures surrounding the subject matter of interest. For example, in nuclear medicine imaging techniques, a radiopharmaceutical is injected into a patient. Specific radiopharmaceuticals are selected to provide images for particular diagnostic imaging tests. Some radiopharmaceuticals concentrate in a particular region of interest, such as the circulatory system, the heart, brain or other organs and causes radiation to be emitted from the region of interest. The radiation emitted from within the patient is detected by the imaging equipment and is used to generate the diagnostic images. The images resulting from nuclear imaging techniques provide substantial information about the region of interest but generally do not show skeletal structures or other nearby organs such as the lungs when the radiopharmaceutical is selected to emphasize the heart. A physician may also require image information about the structure nearby the particular region of interest of the patient to make a more accurate diagnosis or administer a selected treatment.

When a physician requires images of anatomical structure, other medical imaging modalities can be used. For example, anatomical modalities include X-Ray, CT, MRI, ultrasound, portal images and video sequences obtained by various scopes such as laparoscopy or laryngoscopy. Some derivative techniques include magnetic resonance angiography (MRA), digital subtraction angiography (DSA) and computed tomography angiography (CTA). Images obtained from these modalities can be used to provide suitable images for general anatomical structure within an examination region.

When images from more than one imaging modality are available, it is often desirable to combine the information in the separate images from the different modalities into a single image. In addition to multimodality registration and fusion, it is sometimes valuable to combine images from a single modality. Monomodality registration can be useful for treatment verification by comparison of pre and post intervention images, comparison of ictal and inter-ictal (during and between seizures) SPECT images, growth monitoring using time series of MR scans on tumors or X-ray time series on specific bones as well as the area of patient staging, where the patient contour, organ positions and sizes could be different due to time, changes in body habitus, and different acquisition positions and or protocols.

Rather than side by side comparison, the multimodality or monomodality images may be superimposed upon one another to correlate the location of specific image features relative to one another. Superposition of images of specifically related subject matter involves registration of the images and fusion of the images. Registration generally involves spatial alignment of the images and fusion is performed to produce the integrated display of the combined images. The combined or fused images might be, stored, displayed on a computer screen or viewed on some form of hard output, such as paper, x-ray film, or other similar mediums.

Various methods are known for registering images from different imaging modalities. However, registering images with both ease and accuracy is a problem associated with these methods. For example, images can be registered manually by an operator or medical professional. However, this method is generally not very accurate since there is oftentimes insufficient common information between the images to use as reference points.

Another registration method involves the use of markers (fiducials) or stereotactic frames. When using these extrinsic methods, markers or reference frames are placed next to or onto a patient during imaging. The patient is imaged in one modality then transported to the other modality for imaging. The markers or frames are visible in the images to be combined. Precisely fixing the location of the markers relative to the patient's body can be problematic. The patient may move slightly between scans and during scans, and if there is patient movement relative to the markers, it becomes difficult to accurately register the resulting images.

Intrinsic methods rely on patient generated image content. Some examples of these registration methods includes identification of salient points or landmarks, alignment of segmented binary structures such as object surfaces and utilizing measures computed from the image grey values (voxel based).

One of the challenges in image fusion, regardless of the presently available method selected, is that the images may never align well using rigid body registration methods due to physiological movements such as diaphragm motion. This is particularly true when the scan time to acquire image data for a subject is different. For example, a suitable image dataset may be obtained in a single breath hold for a CT image while a PET scan may require many respiratory cycles throughout the data collection period. The physiological motion during the longer nuclear scan can make it difficult to register and fuse the PET and CT images. This motion causes inaccurate registration and fusion of the images.

SUMMARY OF THE INVENTION

The present invention is directed to a method and apparatus for non-rigid registration and fusion of images with physiological modeled organ motions resulting from respiratory motion and cardiac motion. These motions are mathematically modeled with physiological constraints. The various aspects of the present invention satisfies the need to provide registered and fused images which are modified for physiological motion. A method of combining images according to principles practiced in the present invention comprises the steps of obtaining a first image dataset of a region of interest of a subject and obtaining a second image dataset of the region of interest of the subject. Next, a general model of physiological motion for the region of interest is provided. The general model of physiological motion is adapted with data derived from the first image data set to provide a subject specific physiological model. The subject specific physiological model is applied to the second image dataset to provide a combined image.

An apparatus which illustrates aspects of the present invention includes a first memory storing a first image dataset of a region of interest of a subject; a second memory storing a second image dataset of the region of interest of the subject and a general model of physiological motion for the region of interest. The apparatus includes means for adapting the general model of physiological motion with data derived from the first image data set to provide a subject specific physiological model. In addition, means are provided for applying the subject specific physiological model to the second image dataset to provide a combined image.

An apparatus and method applying principles of the present invention provides the foregoing and other features hereinafter described and particularly pointed out in the claims. The following description, claims and accompanying drawings set forth certain illustrative embodiments applying various principles of the present invention. It is to be appreciated that different embodiments applying principles of the invention may take form in various components, steps and arrangements of components and steps. These described embodiments being indicative of but a few of the various ways in which some or all of the principles of the invention may be employed in a method or apparatus. The drawings are only for the purpose of illustrating an embodiment of an apparatus and method applying principles of the present invention and are not to be construed as limiting the present invention.

BRIEF DESCRIPTION OF THE DRAWINGS

The foregoing and other features and advantages of the present invention will become apparent to those skilled in the art to which the present invention relates upon consideration of the following detailed description of apparatus applying aspects of the present invention with reference to the accompanying drawings, wherein:

FIGS. 7A and 7B are transverse and sagittal schematic representations of body and organ movement in response to respiratory motion;

FIGS. 9A and 9B are representations of morphing based on transformation of control points in accordance with principles used with the present invention; and FIGS. 10A and 10B show schematic representations of pixels of image data and the application of motion vectors to the image data according to principles of the present invention.

DETAILED DESCRIPTION

Figure 1:
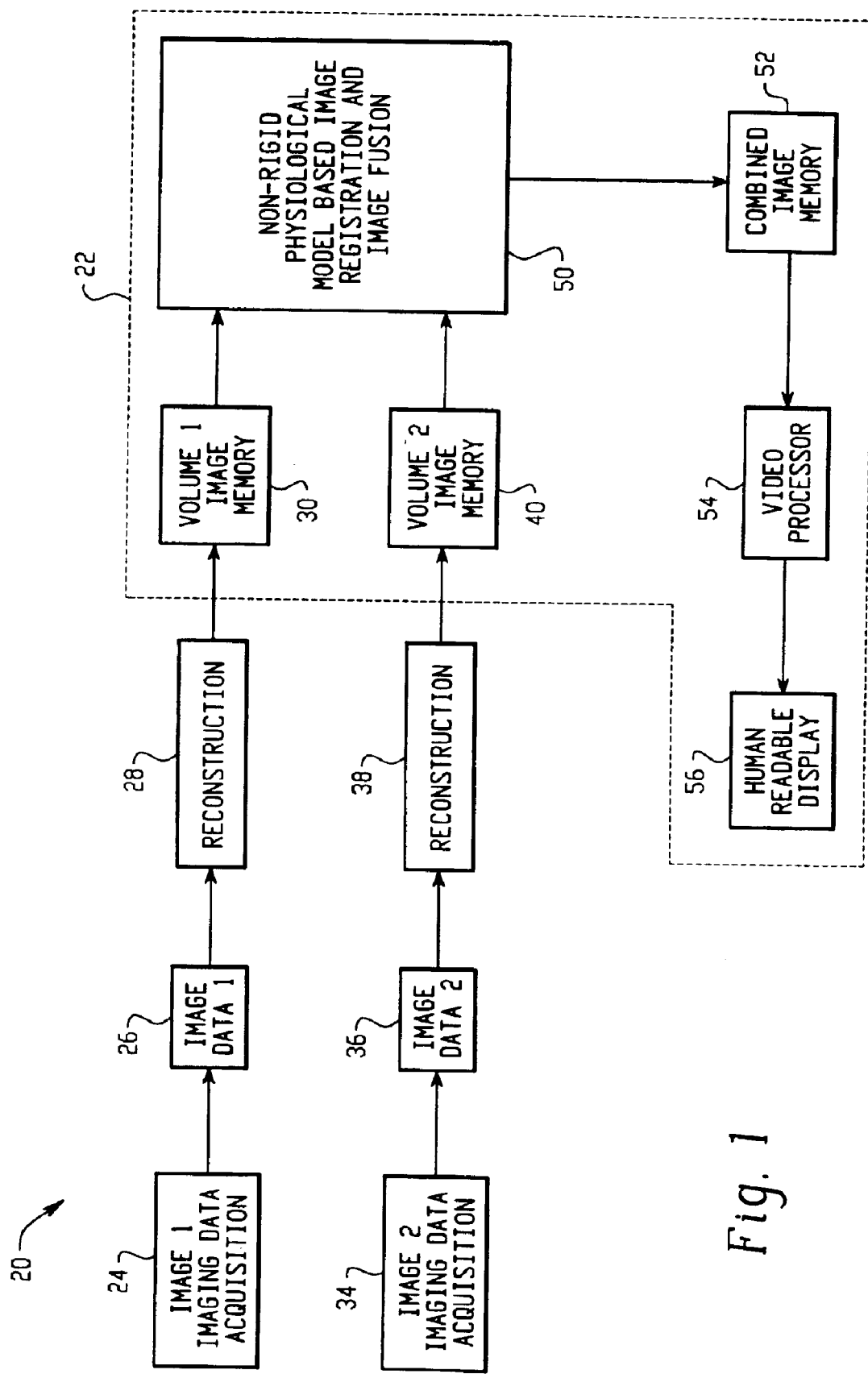
FIG. 1 is a general block diagram of a system for implementing aspects of the present invention.

With reference to FIG. 1, an image registration and fusion process 20 is shown with an image registration and fusion system 22 for providing combined images from two different imaging scans. A first scanning sequence 24 acquires and stores image data 26 in memory. The image data 26 is processed in a suitable reconstruction processor 28 for the particular imaging modality. The reconstructed image is loaded into a volume image memory 30. A second scanning sequence 34 acquires and stores image data 36 in memory. The image data 36 is processed in a suitable reconstruction processor 38. The reconstructed image is loaded into a volume image memory 40. The first and second scanning sequences 24, 34 can be monomodality or multimodality image scanning sequences. The volume image memories 30, 40 can be any suitable data storage device that can be in suitable data communication with the image registration and fusion system 22 including memory such as (i) disks, tape or other magnetic storage, optical or other storage media that is transportable, (ii) memory within a respective imaging system, (iii) image management data storage system as well as (iv) memory within the image registration and fusion system 22.

A non-rigid physiological model based image registration and image fusion processor 50 is in data communication with the volume image memories 30, 40. The image memories 30, 40 input reconstructed image data into the processor 50. The processor 50 provides the registered and fused image, as described below, to a combined image memory 52 which is operatively connected to a video processor 54. The video processor 54 is connected to a human readable display 56 for viewing of the registered and fused images.

Figure 2:
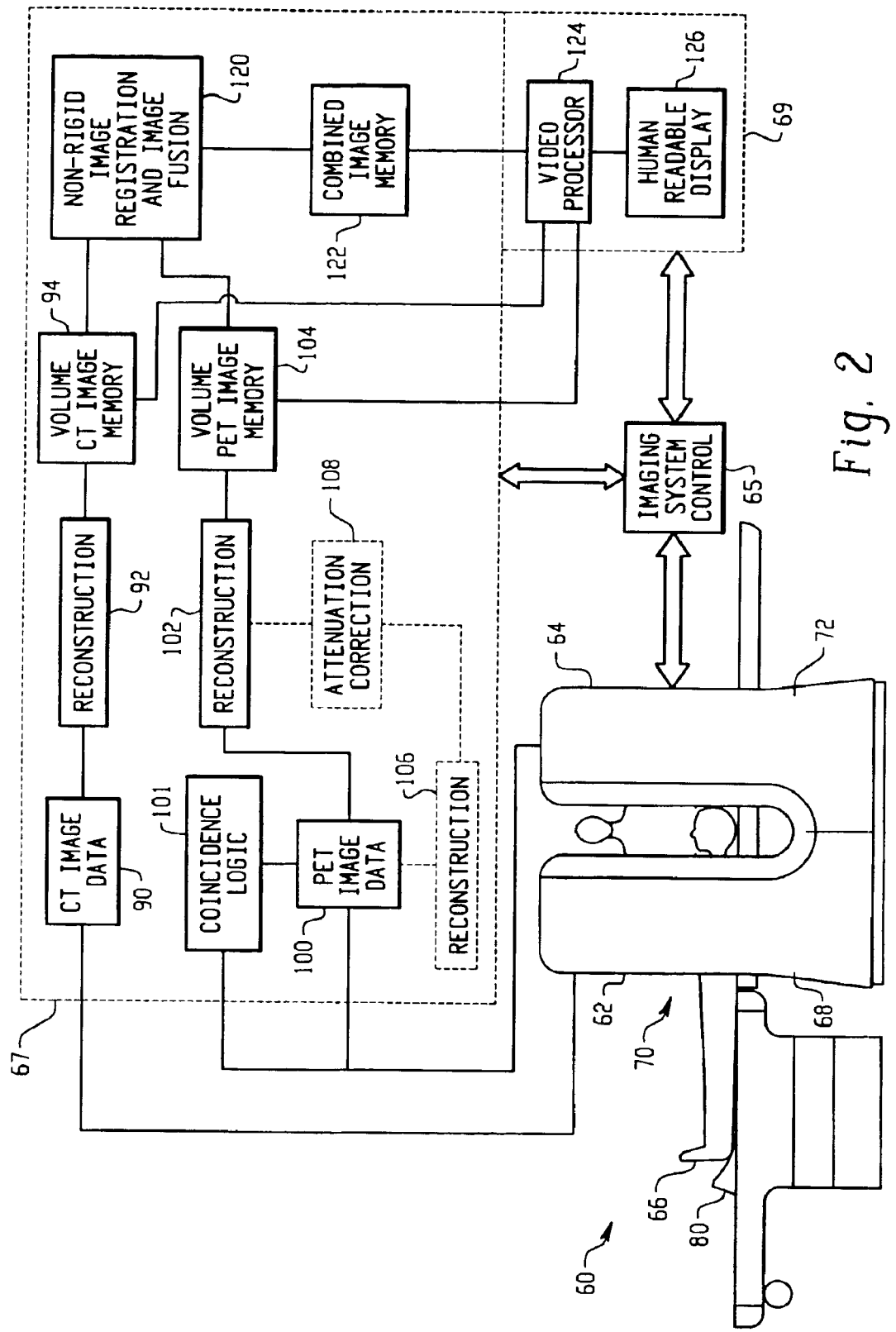
FIG. 2 is a schematic side view of a multimodality medical imaging system incorporating aspects of the present invention.

Turning now to FIG. 2, a multimodality medical imaging system scanner assembly 60 is shown having first imaging device 62 and second imaging device 64, an imaging system control 65, an imaging processor 67 and display system 69. The imaging system control 65 coordinates the physical operation of the scanners 62, 64 as well as the other components of the multimodality scanner assembly 60. All of the control and imaging processing functions in the illustrated components and systems can be performed by known computer based systems having an operable complement of component systems such as suitable processors, memory and storage, input, output and data communications capabilities whether discrete or combined imaging systems as well as remotely located systems in suitable data communication with one another.

The imaging devices 62 and 64 cooperate to obtain patient information through different imaging modalities, to provide anatomical structure images and physiologic function images of a subject 66. More specifically, in this embodiment of an apparatus illustrating principles of the present invention, imaging device 62 is a computed tomogrophy (CT) scanner that utilizes X-rays as the mode of obtaining data from which images depicting the internal structure of the subject 66 are formed. Imaging device 64 is a positron emission tomography (PET) scanner that utilizes positron emissions originating from a radio-pharmaceutical introduced to the patient as the mode of acquiring data from which images depicting primarily metabolic physiological functions within the subject 66 are formed. It is to be appreciated that other suitable combination of imaging modalities described above in the background can be utilized for obtaining multimodality images to be utilized in a system applying principles of the present invention. In addition, it is to be appreciated that the image data sets used in applying principles of the present invention may be obtained from discrete imaging systems in different locations.

The CT scanner 62 includes a floor-mounted, non-rotating gantry 68 whose position remains fixed during data collection. An x-ray tube is rotatably mounted on an internal rotating gantry (not shown). The stationary gantry 68 includes a cylindrically shaped bore that defines a patient examination region 70. An array of radiation detectors are operatively disposed within the gantry cover concentrically around the internal surfaces of patient examination region 70. The detectors are positioned to receive radiation from the x-ray tube which has traversed the examination region 70. Alternatively, an arc segment of radiation detectors can be mounted to the rotating gantry to rotate with the x-ray tube. Data from the detectors of the CT scanner 62 are stored in an image data memory 90 and are reconstructed by a reconstruction processor 92. The reconstructed data are loaded into a volume CT image memory 94.

A subject support table 80 serves as a patient handling assembly and support structure. The table 80 is controlled by the imaging system control 65 to coordinate movement of the subject 66, with respect to operation of the imaging devices 62 and 64, to obtain subject imaging information at one or more desired locations along the length of the subject 66. The table 80 is capable of extending the subject through the respective examination region 70 of the imaging devices 62 and 64 in a variety of methods, such as at a continuous rate, at variable rates, in incremental displacements or a combination of such methods, as may be desired or suitable for image data acquisition.

The PET scanner 64 includes a floor-mounted, non-rotating gantry 72 whose position remains fixed during data collection. The stationary gantry 72 includes a cylindrically shaped bore that further defines the patient examination region 70. An array of known radiation detectors are operatively disposed within the gantry cover concentrically around the internal surfaces of patient examination region 70. The detectors are positioned to receive emission radiation from the subject 66 within examination region 70 that has received a suitable radiopharmaceutical as well as transmission radiation for non-uniform attenuation correction. Data from the detectors of the PET scanner 64 are passed through a coincidence logic processor 101 and qualifying data are stored in an image data memory 100.

In nuclear imaging, radiation that is emitted from various points in the interior of the patient's body must pass through tissue between the emission point and the detector assembly. Some tissue, such as bone, attenuates the radiation data significantly more than other tissue within the subject 66. Accordingly, the emission data is commonly corrected for the greater attenuation attributable to some of the intervening tissue relative to others. In one embodiment of an apparatus that practices aspects of the present invention, data obtained from a transmission source (not shown) and transmitted across the examination region 70 is received by the detectors, sorted and stored in a portion of image memory within the PET image data memory 100. The transmission image data are conveyed to a transmission reconstruction processor 106 and then to an attenuation correction memory 108. Based on the transmission radiation constructed images, the tissue along the trajectory followed by each emission radiation data value collected is determined at an appropriate attenuation correction factor. The reconstruction processor 102 corrects the emission radiation data from PET image data memory 100 in accordance with the determined attenuation factor corrections. The reconstructed data are loaded into a volume PET image memory 104.

The data from the volume CT image memory 94 and volume PET image memory 104 are provided to a non-rigid image registration and fusion process 120. The non-rigid image registration and fusion process 120 performs non-rigid registration of CT and PET images with physiological modeled organ motions, such as respiratory motion and cardiac motion. These physiological motions are mathematically modeled with physiological constraints. The directions of the motions and physical constraints are obtained from some a priori knowledge from other sources, such as dynamic CT or MRI data. By using such constraints, the optimization process will transform the image elastically to a physically meaningful state instead of searching for absolute volume to volume (or surface to surface) error minimization. The process 120 provides the fused image data to a combined image memory 122.

A video processor 124 is operatively connected to the combined image memory 122 to process the image data to provide suitable video signals to a human readable display 126. In addition, the video processor is operatively connected to the volume memories 94, 104 to provide images from each of the imaging modalities 62, 64 for individual display, for visual comparison between one another or with the fused images.

Figure 3:
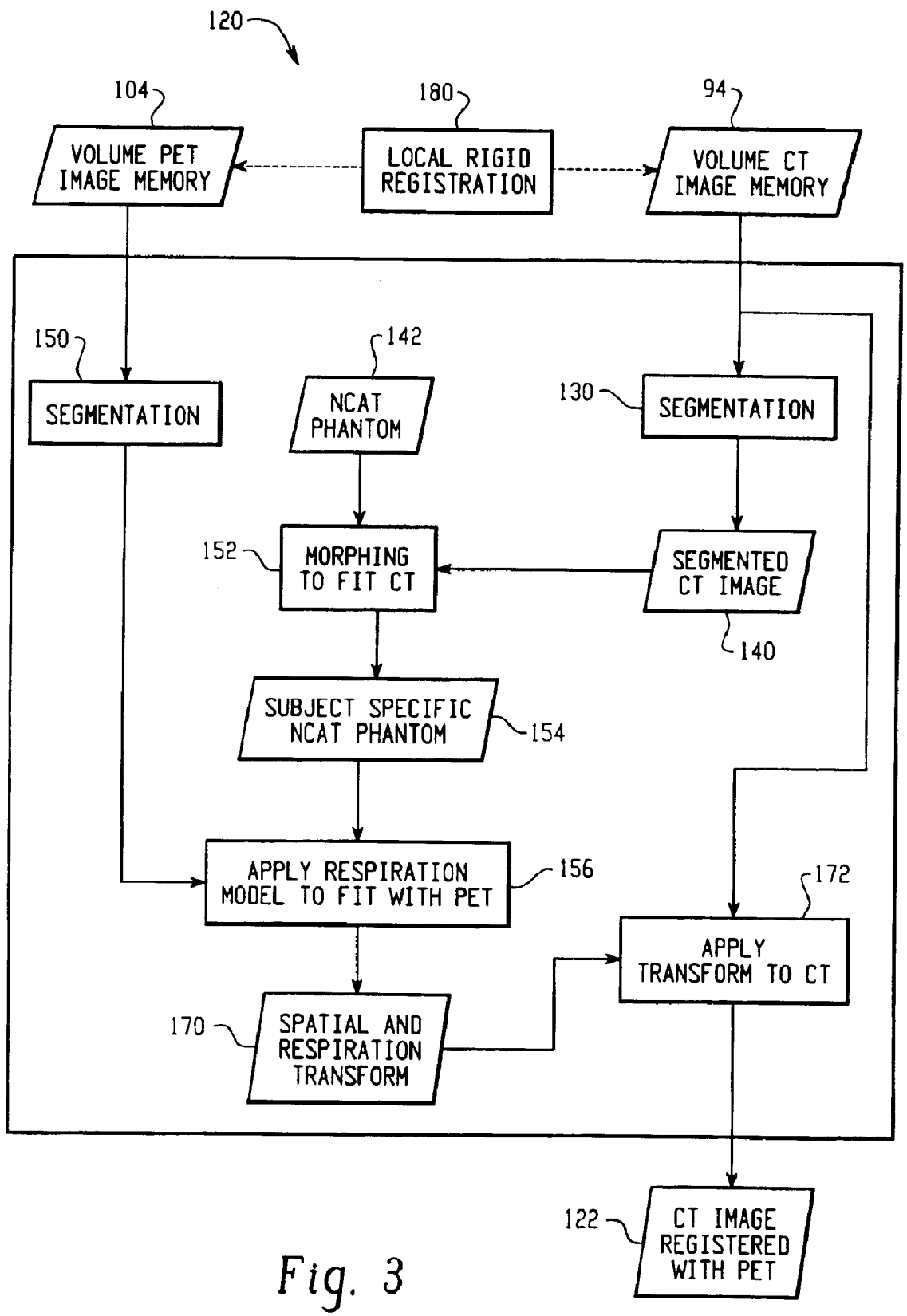
FIG. 3 is a functional block diagram of an embodiment of a method and apparatus illustrating aspects of the present invention.

Turning now to FIG. 3, one process in accordance with principles of the present invention of the non-rigid image registration and fusion process 120 is shown. In this embodiment, the CT image is registered to the PET emission image data providing a non-rigid physiological model based image registration and fusion as well as providing for PET attenuation correction. After registration, the transformed CT data can be converted to a map of attenuation coefficients at the emission energy of 511 keV that can be used for PET attenuation correction. The use of CT images for PET attenuation correction is a well-known technique within the art and description of suitable techniques are provided in Kinahan P E, Townsend D W, Beyer T, and Sashin D, 1998, Attenuation correction for a combined 3D PET/CT scanner, Med. Phys. 25 2046–53 and Guy MJ, Castellano-Smith I A, Flower M A, Flux G D, Ott R J, and Visvikis D 1998, DETECT-dual energy transmission estimation CT-for improved attenuation correction in SPECT and PET, IEEE Trans. Nuclear Sci. 45 1261–67, both of which are incorporated herein by reference.

The process 120 begins with an automatic segmentation step 130 of the volume CT image data in memory 94 to extract surfaces of organs, for example, as well as the body contour and lung contour of the subject or region of interest as desired. These surfaces and contours are used to generate a subject specific Non Uniform Rational B-Spline (NURBS) CArdio Torso (NCAT) phantom model. A threshold-based image segmentation method is used, although, edge based, region based as well as active contour methods are suitable for the segmentation step 130.

Figure 4:
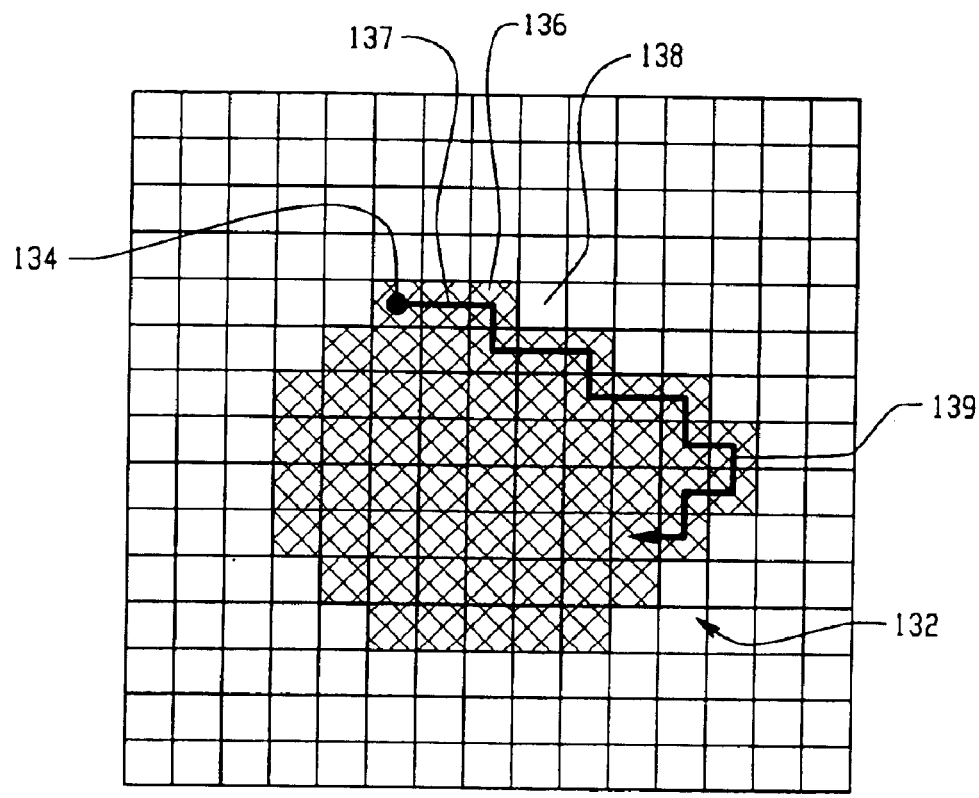
FIG. 4 is a representation of an example of a suitable segmentation technique for use in accordance with aspects of the present invention.

In FIG. 4 the threshold based image segmentation to find an organ or body contour 132 on a pixel by pixel basis is illustrated. The pixels are compared to a threshold value that is suitable for the relevant adjacent body tissue or free space for a body contour. The process is initiated at the first appearance of a pixel 134 having a value greater than the threshold by registering the location of the start pixel 134. The search of pixels for threshold comparison then traces in a clockwise direction, shown by the search pattern 139, from the start pixel 134 to a target pixel 136 such that the pixel 137 to the left of the target pixel 136 has a value equal to or smaller than the threshold and pixels 138 to the right have values greater than the threshold. Each pixel location satisfying the criterion for a contour is stored for segmentation. The iterative process of comparing pixels to the threshold value to determine the contour of the organ or body continues until the contour of the organ or body is closed. For determining the lung contour the pixel values to the left of the target pixel should be greater than the selected threshold value. Upon completion of the CT image segmentation, the segmented CT image is stored 140.

The method applying principles of the present invention includes a general organ-based physiological model 142 of organ and body motion in response to respiratory initiated physiological motion. In the general NCAT phantom model 142, the organ geometry from the average of a subject population is created using Non-Uniform Rational B-Spline techniques.

Figure 5:
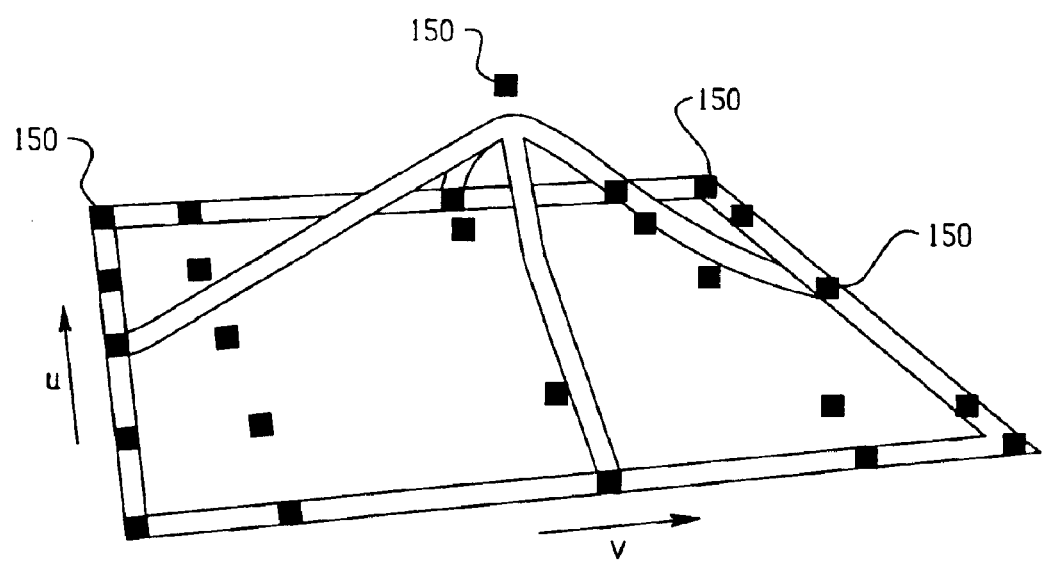
FIG. 5 is a representation of a 3D Non-Uniform Rational B-Spline surface.
Figure 6A:
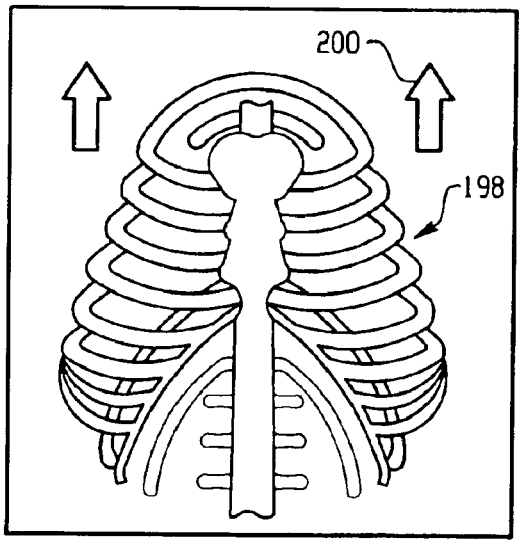
FIGS. 6A, 6B, 6C and 6D are schematic representations of simulated respiratory motion in a 4D NCAT phantom.
Figure 6B:
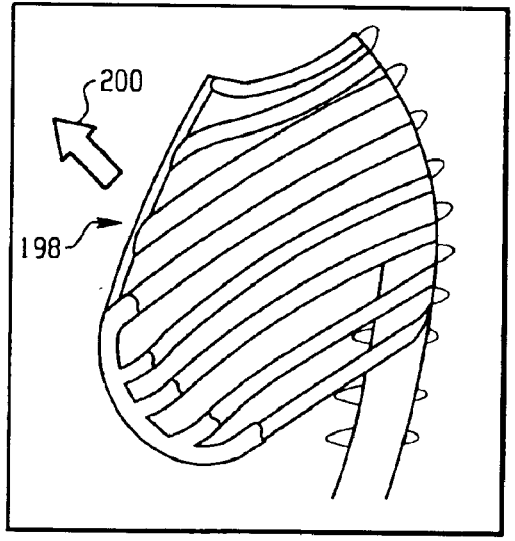
Figure 6C:
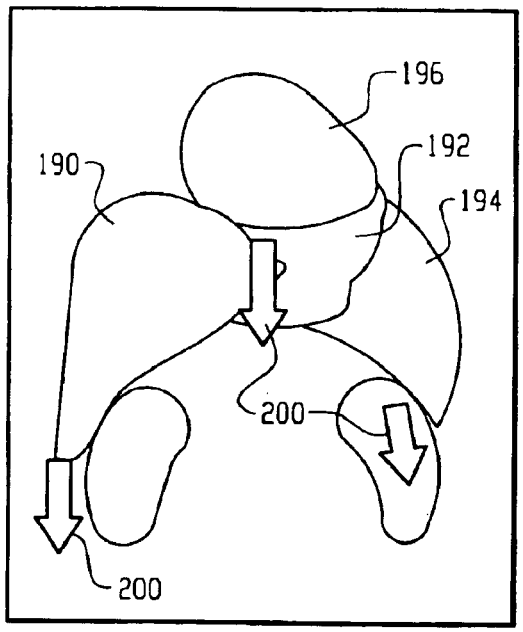
Figure 6D:
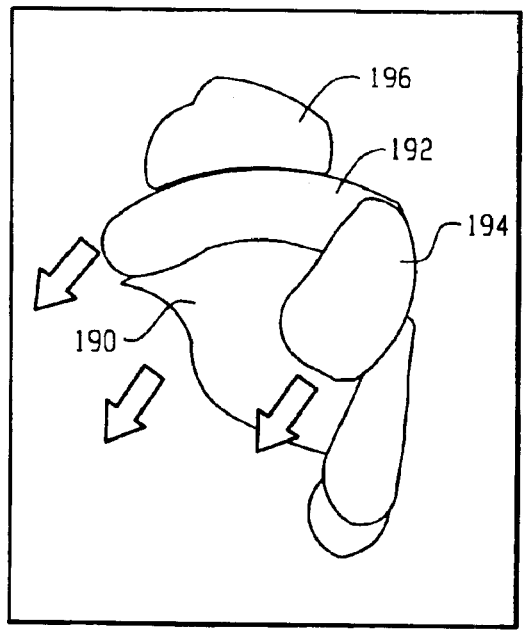

Referring to FIG. 5, non-uniform rational B-splines (NURBS) are mathematical representations of three-dimensional geometry that can accurately describe three-dimensional surfaces. Control points 150 on a NURBS surface are defined by two parametric variables, u and v, usually representing longitude and latitude respectively. A 3D NURBS surface of degree p in the u direction and degree q in the v direction is defined as a piecewise ratio of B-spline polynomials as given by the following function:

$$S(u,v) = \frac{\sum_{i=0}^{n}\sum_{j=0}^{m} N_{i,p}(u) N_{j,q}(v) w_{ij} P_{ij}}{\sum_{i=0}^{n}\sum_{j=0}^{m} N_{i,p}(u) N_{j,q}(v) w_{ij}} \quad (1)$$

where:

S is a point on the surface defined in homogeneous coordinates (x, y, z, 1), n and m are the number of control points in the u and v directions respectively, $P_{ij}$ is the n×m matrix of control points also defined in homogeneous coordinates, $w_{ij}$ are scalar weights that determine a control point's influence on the shape of the surface, and $N_{i,p}(u)$ and $N_{j,q}(v)$ are polynomial functions of degree p and q respectively.

NURBS surfaces provide the flexibility to model complex biological shapes that can be based on subject image data. Furthermore, applying transformations to the control points 150 that define the surface can modify the shape of the NURBS surface. Each transformation is performed by multiplying the control points $P_{ij}$ of the surface to be altered by the appropriate transformation matrix, i.e., $$P_{ij}^{transformed} = MP_{ij}$$

where M is the 4×4 transformation matrix (translation, rotation, and scaling). Each organ, can be represented by one S(u,v). Hence, in the case of subject data at a particular respiratory time point, the NCAT can be considered a sum of the individual organs, i.e., $$NCAT = \sum_{q=1}^{Q} S_q(u,v) \quad (2)$$

where Q is the number of organs. As mentioned above, the change in the shape of NCAT phantom is achieved by applying a transformation matrix $M_i$ to each of the control points describing the surfaces. There are a number of methods useful to obtain these matrices. For example, in one method one assumes a general motion of organs obtained from a given subject or averaged over a given population, In this case, the $M_i$'s can be described mathematically according to the assumed motion. In another suitable method, the $M_i$'s are determined directly for each individual organ by comparing the control points of each organ at two states (e.g., the beginning and the end of the respiratory cycle). In yet another suitable method, there is no one-to-one correspondence between all organs in the initial image and in the targeted image. In this case, a direct transformation can be used to determine the $M_i$'s for the organs that are apparent in both images (as in the second method described above) while a model concept and the adjacent motion information can be used to derive the $M_i$'s for those organs which aren't apparent in both images. These cases will be demonstrated in the following paragraphs.

General simulated inspiratory respiration mechanics in the 4D NCAT phantom is modeled for the movement of the chest rib cage, as well as the diaphragm, lungs and other organs as shown in FIGS. 6A–D. Expiratory motion is simulated as the reverse of the inspiratory motion. The NCAT phantom or similar physiological based models can be used for the purpose of non-rigid registration in this disclosure.

The general physiological model 142 is modified to fit, as described herein, with a specific subject. The motion or shape change of each organ due to respiration, or other motions of the subject, can be characterized by adjusting a few parameters in the modified subject specific model. A suitable general physiological model to be used with subjects is the NCAT model that has been developed at the University of North Carolina. In this model, two parameters, (i) the height of the diaphragm (not shown) and (ii) the anterior-posterior (AP) expansion of the chest, control the respiratory motion in the NCAT phantom. The height of the diaphragm controls the longitudinal motions of the liver 190, stomach 192, spleen 194 and heart 196. The AP expansion of the chest controls the lateral and AP motions of these organs as well as the motion of the ribcage 198. General schematic representations of typical organ and ribcage motions are shown by the arrows 200. The parameters are modified as a function of time as described by equations (3) and (4) in order to form a 4D respiratory model.

$$\Delta Z_{diaphragm}(t) = \begin{cases} 1.0\cos(\frac{\pi}{2}t) + 1.0 & 0 \le t \le 2 \\ 1.0\cos(\frac{\pi}{3}(5-t)) + 1.0 & 2 \le t \le 5 \end{cases} \quad (3)$$

$$\Delta AP_{chest}(t) = \begin{cases} -0.6\cos(\frac{\pi}{2}t) + 1.0 & 0 \le t \le 2 \\ -0.6\cos(\frac{\pi}{3}(5-t)) + 0.6 & 2 \le t \le 5 \end{cases} \quad (4)$$

The liver 190, diaphragm and heart are set to move upward and downward with the change in the height of the diaphragm as described by equation (3). This motion, as with the other translational motions described below, is achieved by applying the appropriate translation matrix M to the control points defining the given organ, e.g., $$P_{i,j}^{translated} = MP_{i,j} = \begin{bmatrix} 1 & 0 & 0 & 0 \\ 0 & 1 & 0 & 0 \\ 0 & 0 & 1 & \Delta Z \\ 0 & 0 & 0 & 1 \end{bmatrix} P_{i,j} \quad (5)$$

The AP motion of these organs were set to follow the expansion of the AP diameter of the chest as described by equation (4) with positive values indicating forward motion. For the stomach, the vertical, AP and lateral motions are given by equations (6)–(8), respectively.

$$\Delta Z_{stomach}(t) = 0.74 \Delta Z_{diaphragm}(t) \quad (6)$$

$$\Delta AP_{stomach}(t) = 1.68 \Delta AP_{chest}(t) \quad (7)$$

$$\Delta lateral_{stomach}(t) = 0.89 \Delta AP_{chest}(t) \quad (8)$$

Similarly, the vertical, AP and lateral motions for the spleen are given by equations (9)–(11), respectively.

$$\Delta Z_{spleen}(t) = 0.63 \Delta Z_{diaphragm}(t) \quad (9)$$

$$\Delta AP_{spleen}(t) = 1.14 \Delta AP_{chest}(t) \quad (10)$$

$$\Delta lateral_{spleen}(t) = 0.95 \Delta AP_{chest}(t) \quad (11)$$

The motion of the ribcage is performed by having each rib rotated about the transverse axis (x-axis) by an angle $\phi_R$ given by $$\phi_R = \arccos\left(\frac{T-C}{L}\right) - \arccos\left(\frac{(T-C) + \Delta AP(t)}{L}\right) \quad (12)$$

where $T=(T_x, T_y, T_z)$ is the coordinate for the tip of the rib, $C=(C_x, C_y, C_z)$ is the coordinate for the tip of the rib's costal neck, L is the AP length of the rib, and $\Delta AP(t)$ is the change in the AP diameter of the chest as a function of time given by equation (4).

The rotation of each rib about the x-axis is performed by applying the appropriate rotation matrix M to the control points defining the rib, i.e., $$P_{i,j}^{rotated} = MP_{i,j} = \begin{bmatrix} 1 & 0 & 0 & 0 \\ 0 & \cos\phi_R & -\sin\phi_R & 0 \\ 0 & \sin\phi_R & \cos\phi_R & 0 \\ 0 & 0 & 0 & 1 \end{bmatrix} P_{i,j} \quad (13)$$

The NURBS surfaces defining the lungs and body outline in this NCAT phantom link their control points to the first nine ribs of the ribcage. For each rib that is rotated, the corresponding control points in the lung and body outline are similarly rotated. In this manner, the shape of these surfaces change in correspondence with the expansion and contraction of the ribcage. This NCAT model is further described in W. P. Segars, Ph.D. thesis entitled Development and Application of the New Dynamic NURBS-Based Cardiac Torso (NCAT) Phantom, Department of Biomedical Engineering, University of North Carolina at Chapel Hill, 2001 which is incorporated herein by reference, and, W. P. Segars et al., Modeling Respiratory Mechanics in the MCAT and Spline-Based MCAT Phantoms, IEEE Transactions on Nuclear Science, Vol. 48, NO. 1, February 2001 which is incorporated herein by reference.

Next, to prepare the volume PET image data to morph to the subject specific NCAT phantom model, an automatic segmentation step 150 of the volume PET image data in memory 104 is completed. A threshold segmentation similar to that described above is performed with threshold values relevant to the volume PET image data. In the case of PET emission data, the body outline is extracted from the image data.

In step 152, the general NCAT physiological phantom is morphed to fit the CT image thereby generating a subject specific physiological model 154. The basic surfaces of the organs extracted from the CT image are fit with smooth, cubic NURBS surfaces to create a new subject specific NCAT phantom. In general, it can be described as a function of the individual NURBS surfaces that model the organs, and the parameters, $p_i$, that describe the respiratory motion i.e., $$NCAT = F(S_1(u,v), S_2(u,v), \ldots S_k(u,v), p_1, p_2, \ldots p_N). \quad (14)$$

The body, lungs, heart, liver and diaphragm are segmented from the CT image and 3D cubic NURBS surfaces are fit to them to create the patient-specific NCAT phantom.

Next, in step 156, the subject specific NCAT phantom of 154 is morphed to fit the segmented PET data of step 150. In general, the morphing process is controlled by the parameters $p_1, p_2, \ldots, p_N$ of the NCAT model. In this case, there is not a one-to-one organ correspondence between the two image sets and some approximations are made to use the NCAT model as described below.

In FIGS. 7A and 7B, the subject specific NCAT phantom from the CT data can be matched to PET emission and/or transmission data. In one implementation of matching the CT subject specific NCAT phantom to PET emission data the parameter $p_1$ is the difference between the anterior-posterior (AP) diameters of the body shown by the arrows 300 and a first body outline 302 and a second body outline 304. The body diameter is determined by sampling points on the body surface at 90° and 270° for a given transaxial slice. The parameter $p_1$ is then determined by averaging the difference of the AP diameters over all slices. The parameter $p_2$ is the change in height of the diaphragm 322 shown by the arrow 320. Since the diaphragm is not visible in the non-attenuation corrected PET emission image, the value of $p_2$ is taken to be 1.5 times $p_1$ in accordance with the NCAT respiratory model. These two parameters control the respiratory motion of the NCAT phantom as follows. The heart, liver and diaphragm are translated in the AP direction by Pi and longitudinally by $p_2$. The body and lungs are scaled in the AP direction by $p_1$ as described in Figure B. The lungs are also scaled longitudinally by $p_2$. This defines the spatial and respiratory transform 170 (FIG. 3) for the subject-specific NCAT. In this case, $p_1$ is equivalent to $\Delta AP_{chest}$ of Equation (4) and $p_2$ is equivalent to $\Delta Z_{diaphragm}$ of Equation (3).

When matching the CT subject specific NCAT phantom to PET transmission data, the parameter $p_1$ is defined and determined as described above. The parameter $p_2$ is defined as above, but since the diaphragm is visible in the PET transmission image, the translational motion of the diaphragm is determined directly by comparing the diaphragm surfaces for the PET and CT images. These two parameters control the respiratory motion of the heart, liver and diaphragm as described above. Two further parameters are considered for the motion of the lungs. The parameter $p_3$ is the AP scaling factor shown by the arrow 340 for each lung 342 and the parameter $p_4$ is the lateral scaling factor shown by the arrow 360 for each lung. Unlike a global AP scaling factor for the body, the lung scaling factors are determined for each lung and applied on a slice by slice basis. As in the previous case, the body is scaled in the AP direction by $p_1$. This defines the spatial and respiratory transform 170 (FIG. 3) for the subject-specific NCAT.

Turning now to FIGS. 9A and 9B, an example is shown of morphing based on the transformation of control points 374. In FIG. 9A, the transformation can be based on a single parameter such as anterior-posterior difference between body outlines 370, 372. The scaling is achieved through a suitable shift of each control point 374 to a transformed control point location 375 with the shift represented by arrows 376 and being proportional to the distance of the control point from the origin of the scaling 380. In FIG. 9B, the transformation includes lateral scaling as well represented by the arrows 378. The motion of the control points 374 includes multidirectional components as shown by the illustrated resultant arrows 378.

Next, in step 172, the transform 170 is applied to the volume CT image data 94. More specifically, the motion vectors used to transform the subject specific NCAT model to match the PET data are applied to the CT volume image data. Turning to FIGS. 10A and 10B, surfaces of the body outline 400, lungs 410, 420, and heart 430 for the subject specific NCAT model of step 154 (FIG. 3) are represented with solid lines. Motion vector 435 depicts the translation of the heart 430. Scaling of the lungs 410, 420 is shown by the vectors 415, 425 respectively and scaling of the body outline 400 is shown by vector 405. These vectors depict translation of the body and organs in the AP direction and are used to transform the subject specific NCAT model of step 154 to match the PET data 600 from step 150 according to the respiratory model in step 156. The surfaces of the body outline 500, lungs 510, 520, and heart 530 for the transformed NCAT model of step 154, that is now aligned with the PET data 600, are represented with dashed lines in FIG. 10A.

To align the CT image volume data from memory 94 to the 4D subject specific physiologically modeled transformed CT data, the same motion vectors that are used to transform the subject specific NCAT phantom of step 154 to match the PET data are applied in step 172 to the pixels of the CT volume image data stored in memory 94. For example, in FIG. 1A, the shaded pixel 432 within the heart 430 of the NCAT model is translated in the AP direction by an amount equal to the heart translation motion vector 435. The same transformation is applied to the corresponding pixel in the CT volume image data. Similarly, pixels in the lung regions will be scaled according to the lung scaling factors 415, 425 while pixels in the body region will be scaled according to the body scaling factor 405. A three dimensional motion vector is determined for the pixels and then the motion vectors are smoothed in 3D before they are applied to the CT volume image data. Upon completion of the application of the transform 170 to the CT data from 94, the combined registered and fused image is stored in the combined image memory 122.

In the event that the imaging modalities are discrete systems and the volume image data of 94, 104 are acquired in different clinical settings (as opposed to the case of a combined CT/PET system shown in FIG. 2), a pre-registration step 180 is performed to rigidly align the volume CT image in 94 with the volume PET image in 104 before non-rigid registration occurs in 120. The rigid transformation is obtained by considering regions of the body that can be considered rigid (i.e., regions of the body that are relatively insensitive to respiratory motion). This pre-registration of image data from discrete imaging systems is also referred to as local registration herein in order to distinguish the pre-registration from conventional rigid registration of images. Any number of known rigid registration algorithms can be applied as the similarity measure, such as mutual information, local-correlation and cross-correlation in combination with various optimization techniques. One suitable combination of techniques for rigid registration and optimization includes the use mutual information registration with simple gradient optimization.

Figure 8:
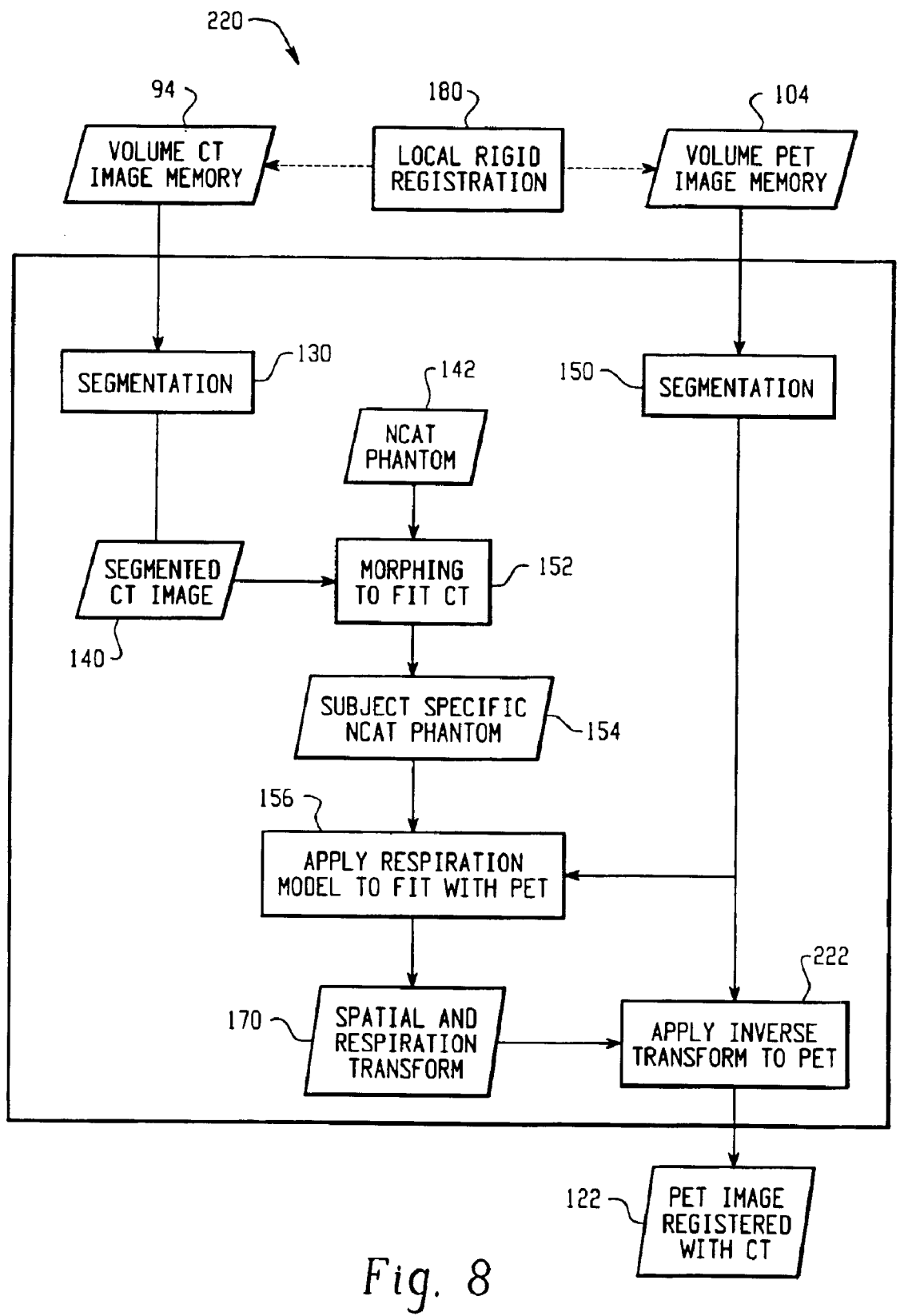
FIG. 8 is a functional block diagram of another embodiment of a method and apparatus illustrating aspects of the present invention.

Turning now to FIG. 8, another non-rigid image registration and fusion process 220 is shown that applies principles of the present invention. Steps and processes similar to the process 120 of FIG. 3 are numbered similarly and are not further described. The process 222 registers the PET image to the CT image without generating an attenuation map for attenuation correction of the PET data with the CT data. As such, in the case of PET emission data, the body outline is extracted from the image data. In the case of PET transmission data, the body outline, lungs, top of the liver, and diaphragm are segmented from the image data. Referring briefly to FIG. 2, the PET data is attenuation corrected using steps 106 and 108 to provide an attenuation corrected volume PET image in the memory 104. Referring to step 222, once the transform parameters from the subject specific model have been determined as described for 154 above, the CT-defined subject specific NCAT model is transformed to match the PET data in step 156 to create a model for the PET data (PET-NCAT).

Referring again to FIGS. 10A and 10B, the surfaces of the body outline 500, lungs 510, 520, and heart 530 for the transformed NCAT are the PET-NCAT model. The pixels in the PET-NCAT have undergone a known motion as described as part of step 172. For example, the shaded pixel 432 within the heart of the NCAT model has been translated in the AP direction by an amount equal to the heart translation motion vector 435 and now corresponds to a specific pixel 532 in the heart of the PET-NCAT. The pixel 532 corresponds to the a pixel 632 in the PET data. To match the PET-NCAT, as shown in FIG. 8 to the original subject specific NCAT, the pixel 532 undergoes an inverse transformation of the heart translation motion 435, i.e., it is translated in the opposite direction of the original translation 435 described above with respect to FIG. 3. Similarly, pixels in the in the lung regions of the PET-NCAT are scaled by the inverse factor of the lung scaling factors 415, 425. Accordingly, pixels in the body region are scaled by the inverse of the body scaling factor 405. Thus, the three dimensional inverse motion vectors for the pixels can be determined. Using the PET-NCAT as a map for the PET volume image data in memory 104, the pixels in the PET volume image data 600 is transformed according to the motion vectors determined from the PET-NCAT. As in the previous example, the motion vectors are smoothed in 3D before they are applied to the PET volume image data.

While a particular feature of the invention may have been described above with respect to only one of the illustrated embodiments, such features may be combined with one or more other features of other embodiments, as may be desired and advantageous for any given particular application. From the above description of the invention, those skilled in the art will perceive improvements, changes and modification. Such improvements, changes and modification within the skill of the art are intended to be covered by the appended claims.

Having described a preferred embodiment of the invention, the following is claimed:

1. A method of combining images, the method comprising the steps of:
   obtaining a first image dataset from a subject;
   obtaining a second image dataset from the subject;
   segmenting the first image data set;
   segmenting the second image data set;
   providing a physiological model;
   morphing the physiological model to the segmented first image data set to produce a subject specific physiological phantom;
   registering the subject specific physiological phantom with the segmented second image data set to generate a transform; and
   applying the transform to one of the first and second image data sets to provide a fused image.

2. A method of combining images, the method comprising the steps of:
   obtaining a first image dataset of a region of interest of a subject;
   obtaining a second image dataset of the region of interest of the subject;
   providing a general model of physiological motion for the region of interest;
   adapting the general model of physiological motion with data derived from the first image data set to provide a subject specific physiological model; and
   applying the subject specific physiological model to the second image dataset to provide a combined image.

3. The method of combining images of claim 2 wherein the first image dataset is obtained from a first imaging modality and the second image dataset is obtained from a second imaging modality different than the first imaging modality.

4. The method of combining images of claim 3 wherein one of the first and second image datasets is primarily functional image data and the other image dataset is primarily anatomical image data.

5. The method of combining images of claim 2 wherein the first image dataset is obtained from a discrete imaging and the second image dataset is obtained from a discrete imaging system.

6. A method of combining images, the method comprising the steps of:
   obtaining a computed tomography image dataset from a subject;
   obtaining a nuclear medicine image dataset from the subject;
   segmenting the computed tomography image data set;
   segmenting the nuclear medicine image data set;
   providing a general physiological model;
   morphing the physiological model to the segmented computed tomography image data set to produce a subject specific physiological phantom;
   registering the subject specific physiological phantom with the segmented nuclear medicine image data set to generate a transform; and
   applying the transform to the computed tomography image data set to provide a fused image.

7. A method of combining images, the method comprising the steps of:
   obtaining a computed tomography image dataset from a subject;
   obtaining a nuclear medicine image dataset from the subject;
   segmenting the computed tomography image data set;
   segmenting the nuclear medicine image data set;
   providing a general physiological model;
   morphing the physiological model to the segmented computed tomography image data set to produce a subject specific physiological phantom;
   registering the subject specific physiological phantom with the segmented nuclear medicine image data set to generate a transform; and
   applying the inverse of the transform to the segmented nuclear medicine image data set to provide a fused image.

8. An image registration and fusion system, the system comprising:
   a first image memory for storing a first image data set of a region of interest of a subject;
   a second image memory for storing a second image data set of the region of interest of the subject;
   a general physiological model for physiological activity relative to the region of interest; and
   an image registration and fusion processor, the processor in operative relationship with the first image memory, the physiological model and the second image memory, the image registration and fusion processor being programmed to:
      morph the general physiological model to the first image data set to produce a subject specific physiological phantom,
      register the subject specific phantom to the second data set to generate a transform, and
      apply the transform to one of the first and second image data sets.

9. The system of claim 8 wherein the physiological model is empirically obtained from image data from an imaging scan of a subject.

10. The system of claim 8 wherein the physiological model a compilation of features from image data from an imaging scans of a plurality of different subjects.

11. The system of claim 8 wherein the processor is further programmed to:
   segment the first image data set prior to morphing the physiological model, such that the physiological model is morphed to the segmented first image data set.

12. The system of claim 11 wherein the processor is further programmed to:

segment the second image data set, prior to registering to the subject specific phantom, such that the segmented second image is registered to the subject specific transform.

13. The system of claim 12 wherein the subject specific physiological model models motion of the subject in response to physiological motion over time.

14. The system of claim 13 wherein the physiological motion is at least one of respiratory motion and cardiac motion.

15. The system of claim 12 further including:

a first imaging modality which generates the first image data set; and a second imaging modality different than the first imaging modality which generates the second image data set.

16. The system of claim 15 wherein the first and second imaging modalities each include a different one of scintigraphy, functional MRI (fMRI), single photon emission computed tomography (SPECT), positron emission tomography (PET), perfusion MRI (pMRI), functional CT (fCT), electro impedance tomography (EIT), magnetic resonance elastography (MRE), X-Ray, computed tomography (CT), magnetic resonance imaging (MRI), ultrasound, laparoscopic and laryngoscopic images, magnetic resonance angiography (MRA), digital subtraction angiography (DSA) and computed tomography angiography (CTA).

17. The system of claim 15 wherein one of the first and second imaging modalities generate data that is primarily functional and the other imaging modality generates data that is primarily anatomical.

18. The system of claim 15 wherein the first imaging modality is a discrete imaging system and the second imaging modality is a discrete imaging system.

19. The system of claim 18 including wherein the processor is further programmed to perform the step of:

pre-registering the first and second image datasets obtained from the discrete imaging systems.

20. The system of claim 12 wherein the step of applying the transform is an inverse application of the transform.

21. The system of claim 12 wherein the general physiological model is a non-uniform rational B-spline cardiotorso phantom model.

22. An apparatus for combining images, the apparatus comprising:

a first memory storing a first image dataset of a region of interest of a subject;

a second memory storing a second image dataset of the region of interest of the subject;

a non-subject specific model of physiological motion for the region of interest;

means for adapting the non-subject specific model of physiological motion with data derived from the first image data set to provide a subject specific physiological model; and means for applying the subject specific physiological model to the second image dataset to provide a combined image.

23. An apparatus for combining images, comprising:

means for obtaining a first image dataset from a subject;

means for obtaining a second image dataset from the subject;

means for segmenting the first image data set;

means for segmenting the second image data set;

means for providing a physiological model;

means for morphing the physiological model to the segmented first image data set to produce a subject specific physiological phantom;

means for registering the subject specific physiological phantom with the segmented second image data set to generate a transform; and means for applying the transform to one of the first and second image data sets to provide a fused image.

24. An apparatus for combining images, comprising:

means for obtaining a first image dataset of a region of interest of a subject;

means for obtaining a second image dataset of the region of interest of the subject;

means for providing a general model of physiological motion for the region of interest;

means for adapting the general model of physiological motion with data derived from the first image data set to provide a subject specific physiological model; and means for applying the subject specific physiological model to the second image dataset to provide a combined image.

* * * * *